United States Patent [19]

Ertl

[11] 4,092,981
[45] June 6, 1978

[54] METHOD AND APPARATUS FOR BRAIN WAVEFORM EXAMINATION

[76] Inventor: John Paul Ertl, 42 Halford Ave., Toronto, Ontario, Canada

[21] Appl. No.: 705,400

[22] Filed: Jul. 15, 1976

[51] Int. Cl.$^2$ .............................................. A61B 5/04
[52] U.S. Cl. .............................................. 128/2.1 B
[58] Field of Search .......................... 128/2.1 B, 2.1 R

[56] References Cited

U.S. PATENT DOCUMENTS

| | | | |
|---|---|---|---|
| 3,760,796 | 9/1973 | Baessler et al. | 128/2.1 B |
| 3,890,957 | 6/1975 | Freeman | 128/2.1 B |
| 3,978,847 | 9/1976 | Fehmi et al. | 128/2.1 B |

OTHER PUBLICATIONS

Marsoner et al., "Medical & Biological Engineering," vol. 8, No. 4, Jul., 1970, pp. 415–418.

Paskewitz, "Psychophysiology," vol, 8, No. 1, Jan., 1971, pp. 107–112.

Emide et al., "Electroencephalography and Clinical Neurophysiology," vol. 37, No. 2, Aug., 1974, pp. 185–187.

*Primary Examiner*—William E. Kamm

[57] ABSTRACT

A neural efficiency rating is arrived at by amplifying and band-limiting an EEG waveform of a subject, discarding those parts of the waveform during which alpha rhythm is present, and measuring the average frequency of the remainder of the waveform. By comparing the phases and amplitudes of the waveforms produced by opposite sides of the subject's brain, abnormalities of brain function may be detected, which together with the neural efficiency rating serves to evaluate brain function.

13 Claims, 1 Drawing Figure

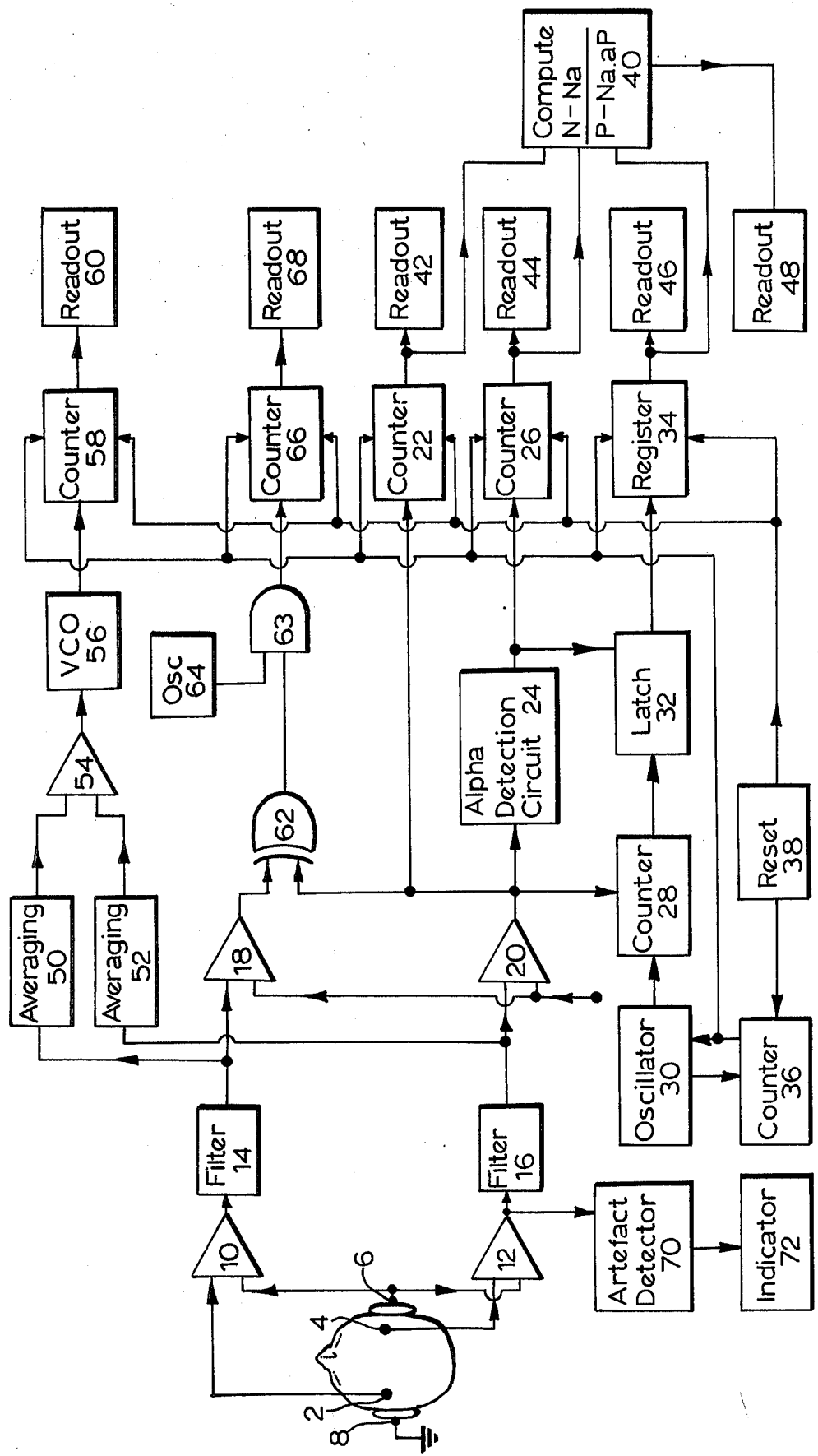

METHOD AND APPARATUS FOR BRAIN WAVEFORM EXAMINATION

FIELD OF THE INVENTION

This invention relates to a method and apparatus for analyzing complex waveforms, and in particular waveforms having an intermittently occurring unwanted component of high amplitude relative to the remainder of the waveform. A particular field of usefulness of the invention is in analyzing E.E.G. (electroencephalograph) waveforms in order to provide an assessment of the functional efficiency of the human or animal brain.

REVIEW OF THE PRIOR ART

Numerous attempts have been made in the past to analyze EEG waveforms in order to arrive at some form of quantitative assessment of the quality of human brain function, but these have not been very successful. Thus whilst it is readily possible to establish correlations between the EEG waveform of a subject and the nature of physical and mental activities carried on by the subject, it has been more difficult to arrive at any assessment of the quality of the brain function involved. Prior U.S. Pat. Nos. 3,498,287 and 3,893,450 issued to J. Ertl Mar. 3, 1970 and July 8, 1975 respectively, proposed techniques for analyzing the response (in terms of EEG waveform) evoked by external stimuli applied to a subject, and thus obtaining an assessment of brain function. However, quite complex techniques are required both in recovering and processing the require data, and it is necessary to process data from a repeated series of evoked responses in order to be able to recover the desired data which in any single instance may be masked by responses to other random stimuli and general brain activity. Moreover, it is necessary to apply empirical correction factors to allow for the proportion of time during the test series that alpha rhythm is present in order to avoid misleading results.

SUMMARY OF THE INVENTION

I have now found that at least as reliable assessment of brain function can be obtained without the necessity of evoking responses and attempting to isolate the actual components of the EEG waveform attributable to such responses. In this technique, an EEG waveform of a subject is continuously sensed, amplified and band limited by conventional techniques, those portions of the waveform occurring during the presence of alpha waves are discarded, and at least one frequency related parameter of the remainder of the waveform is determined. The parameter determined is preferably the average frequency of a function thereof. Alpha waves have a frequency lying within well defined limits, and it is of course possible to filter EEG waveforms so as to remove components lying within these frequency limits: this is not what is done in the present invention. For the purposes of the present invention it is important that those portions of the EEG waveform where alpha rhythm is present be effectively disregarded. Mere filtering will not provide the same result, since other components present simultaneously with the alpha waves will remain to confound the results obtained. Moreover, it is difficult to provide a low frequency band stop filter having a sufficiently sharp roll-off at the edges of the stop-band to stop alpha frequency without significantly attenuating wanted frequencies and without grossly distorting wanted portions of the EEG waveform due to non-linear phase response in the pass-bands, thus rendering reliable analysis difficult or impossible.

Preferably the average frequency of the band-limited EEG waveform is determined by determining the average number of periods per unit time into which the waveform is divided by the zero crossings of the waveform, and the necessary elimination from the result of those parts of the waveform occurring in the presence of alpha rhythm can be achieved by determining how many periods between alternate zero crossings have the same periodicity as a waveform within the frequency band characteristic of alpha events. The number of these latter periods and the sum of their duration is deducted from the total number of periods and their total duration before the required average is calculated. Since the periodicity of an alpha event varies only within a comparatively narrow range, the sum of their durations of a number of such events may be arrived at with a reasonable degree of accuracy merely by multiplying the number of events by a constant, typically 0.111 for junior school children, to arrive at an answer in seconds, although direct measurement is preferred.

Thus the desired average frequency which is utilized as a measure of brain function or neural efficiency may be expressed by the formula $$(N - Na)/(P - Na.aP)$$

where P is the duration in seconds of a timed portion of an EEG waveform being analyzed, N is the number of cycles as delimited by the alternate zero crossings in that portion of waveform, after band limiting, $Na$ is the number of such cycles occurring during the presence of alpha rhythm, as determined by identifying alternate zero crossings separated by periods characteristic of alpha rhythm, and $aP$ is the average periodicity of an alpha event. $aP$ or $Na.aP$ may be determined by direct measurement, or $aP$ may be represented by an appropriate constant value, for example 0.111 seconds.

It should be appreciated that the average frequency arrived at need not be utilized directly as an index of neural efficiency and other forms of index may be preferred which are functions of this frequency and/or are weighted by other constants or variables. Moreover, the results obtained will be influenced by the nature of the band limiting applied to the EEG waveform. Furthermore, in most normal subjects, the sub-alpha frequencies do not form a significant component of the EEG waveform. Useful results may therefore be obtained by rejecting all frequencies below the upper edge of the alpha frequency band. The present invention is predicated on the discovery that the frequency of an EEG waveform, in which those portions occurring during alpha events are discarded, is a variable which is indicative of the neural efficiency of a subject, and the value of this discovery is not diminished by the probability that other variables may also be found to be indicative of neural efficiency or that there may be advantages in weighting the value of average frequency obtained in various ways either by adjusting the waveband analyzed, introducing correction factors, or adopting functions of the frequency concerned. All such variants are within the scope of the invention insofar as they incorporate the basic features of the invention as set out above and defined in the appended claims.

The neural efficiency rating discussed above is rendered of more value when associated with other data indicative of the presence of abnormalities of brain function. I have found two factors which can be used as indicators of such abnormality, and which can conveniently be measured at the same time as neural efficiency, namely the phase difference between EEG waveforms obtained from corresponding areas on opposite sides of the brain and the amplitude difference between such waveforms, there being correlations between abnormal values of these differences and abnormal educational performance.

SHORT DESCRIPTION OF THE DRAWINGS

A preferred embodiment of the invention is described with reference to the accompanying drawing, showing a block schematic diagram of apparatus in accordance with the invention.

DESCRIPTION OF THE PREFERRED EMBODIMENT

The drawing shows a brain wave analyzer receiving EEG waveforms from two electrodes 2, 4. The electrodes may conveniently be mounted on a headband (not shown), so that when the latter is placed over the head of a subject, the electrodes contact the scalp of the subject adjacent corresponding regions on opposite sides of the brain, typically the left and right motor areas. A reference electrode 6 is attached to one ear of the subject and a ground electrode 8 to the other, and the electrodes 2 and 4 are connected, together with the reference electrode 6 to the inputs of identical EEG amplifiers 10, 12 which may be of conventional design. The outputs of the amplifiers are passed to active filters 14, 16 which may also be implemented by conventional techniques. The filters act to band-limit the EEG waveforms, so as to exclude frequencies at which the signals picked up are likely to consist predominantly of signals not due to brain activity. A bandwidth of 4–40 Hz is preferred, but there is latitude to adjust the upper and lower cut-off points both upwardly and downwardly provided that it is appreciated that this will influence the results obtained. A notch filtering means included in each filter 14, 16 to eliminate any mains hum picked up, and is tuned to 60 Hz or 50 Hz depending on the electrical supply frequency used in the area in which the apparatus is to be used.

The outputs of the filters are applied to comparators 18, 20 together with a reference potential selected so that the comparators act substantially as zero crossing detectors; however, the comparators are arranged to have a small degree of hysteresis, sufficient to ensure that they do not react to noise introduced by the EEG amplifiers. The comparators provide a rectangular wave output of which the periodicity of each complete cycle, referred to for convenience as an event, indicates, essentially, the dominant frequency of the corresponding part of the band-limited EEG waveform. Where the periodicity of each complete cycle lies between 83 and 143 milliseconds, corresponding to a frequency range of 7–12 Hz, alpha waves are considered to be present. Any such complete cycle may be referred to for convenience as an alpha event. There is latitude to vary the nominated alpha frequency band, if the subjects being tested show a statistical distribution of alpha wave frequencies which justifies such variation.

Whilst outputs from both channels are required for purposes discussed further below, the output of either channel may be utilized for the purpose of arriving at a neural efficiency rating. In the embodiment shown, the output of the comparator 20 is applied to three different processing channels.

In the first channel, a counter 22 counts the events in the comparator output.

In the second channel, an alpha detection circuit 24 is provided which produces an output pulse only when the commencement of a second event, as marked by either a positive or a negative going zero crossing, follows the commencement of a first event by more than 83 but less than 143 milliseconds, i.e. the first event is an alpha event. This may be achieved by using a first monostable multivibrator to generate short pulses from the selected edges of the rectangular wave output from the comparator 20, i.e. from alternate zero crossings of the waveform, applying these pulses to a retriggerable monostable multivibrator having an 83 millisecond time constant, triggering a third monostable multivibrator having a 60 millisecond time constant from the trailing edges of the output pulses of the second monostable multivibrator, using the pulses from the first monostable multivibrator to gate the output of the third monostable multivibrator, and then after a short delay (set by a fourth monostable multivibrator) sufficient to provide a satisfactory output pulse from the gate, using said pulses to clear the third monostable multivibrator. Such a circuit can only produce an output pulse when the selected edges of the input waveform are spaced by between 83 and 143 milliseconds, thus denoting an alpha event. The output pulses are counted by a counter 26.

In the third channel, the commencement of each successive event is used to clear a counter 28, using the output of the first monostable multivibrator mentioned in the alpha detection circuit 24. The counter receives pulses from a clock oscillator 30 which conveniently has an output frequency of 1 kHz so that the counter counts milliseconds. The outputs of the counter are applied to a latch circuit 32 which is controlled by the output from the alpha detection circuit 24 so as only to pass the count of the counter to an accumulation register 34 when it receives a pulse from the detection circuit 24 indicating that an event whose duration has been counted by the counter 28 is an alpha event. The total count accumulated in the register 34 thus represents, in milliseconds, the total duration of alpha events which have occurred since the register was cleared.

The output of oscillator 30 is also applied to another counter 36 which acts as a timer, and is provided with manually controllable resetting means 38 which also acts to clear the counters 22 and 26 and register 34. On reaching a certain count, conveniently 10,000 representing ten seconds, the counter 36 disables the output of the oscillator, the counters 22 and 26 and the register 34, and a computing device 40 is used to carry out the following computation:

$$(N - Na)/(P - Na.aP)$$

where
$P$ is the period of the timer,
$N$ is the number of events registered by the counter 22 during the period P,
$Na$ is the number of alpha events registered by the counter 26 during the period P, and
$aP$ is the average duration of the alpha events.

Since the total duration of the alpha events during a period P will be $Na.aP$, this latter term can be obtained directly from the register 34. The register may if desired be arranged to subtract the counts received from the latch circuit from P, thus providing the term (P − N$a$.$a$P) directly. Similarly, the counter 22 may be replaced or supplemented by a counter with its input gated by the output of the circuit 24 so as only to count events which are not alpha events, thus giving the term (N − N$a$) directly. The computing device then merely requires to divide the term from the counter by the term from the register in order to satisfy the formula.

A similar result may be obtained by arranging the latch 32 to pass to the register only those counts associated with events which are not alpha events, and the counter 22 only to count non-alpha events, and sensing the accumulated count in the register so as to disable the counter 22 when the register count reaches a predetermined level. With this arrangement, the count accumulated by the counter 22 is directly proportional to the mean frequency of the non-alpha events and no further computation is required.

The result obtained with all the above techniques is the average frequency of events occurring during the period P when alpha events are disregarded, i.e. a close approximation to the average frequency of those portions of the band limited EEG waveform in which alpha rhythm is not present. There is some degree of error since odd half cycles at the beginning or end of an alpha rhythm may be missed, but this is not believed significant.

Preferably, the counts accumulated by the counters 22 and 26 and the register 34 are displayed by digital readouts 42, 44, 46 using conventional techniques, and the output of the computing device 40 is similarly displayed by a digital readout 48 to give a direct indication of neural efficiency.

By taking the readings of readouts 42, 44, 46 at the conclusion of a period P, the computation referred to above may be carried out independently. In one embodiment of the invention, a simple digital calculator of conventional construction is built into the apparatus, and the various counts are transferred from the readouts to the calculator keys by an operator. Alternatively, an analogue calculator in the form of a nomogram may be employed by an operator to carry out the computation.

Besides ascertaining neural efficiency as described above, it is desirable that the presence be ascertained of common abnormalities of brain function which might prevent realization of the potential indicated by the neural efficiency rating alone. Such abnormalities of function include abnormal differences in amplitude and phase between the EEG waveforms from opposite sides of the brain.

In order to compare these amplitudes, the outputs of the filters 14, 16 are applied to averaging circuits 50, 52 in which they are subjected to full-wave rectification and integration using a long (e.g. 5 second) time constant so as to obtain a mean RMS amplitude, and thence to the inputs of a differential amplifier 54. The output of amplifier 54 is used to increase or decrease (according to polarity) the frequency of a voltage controlled oscillator 56 whose output in turn is applied to a counter 58. The count of the counter 58 is shown on a digital display 60 and at the end of a predetermined period, conveniently the period P, provides a measure of the difference of the RMS amplitude of the waveforms obtained from opposite sides of the brain.

The rectangular wave outputs of the comparators 18, 20 are applied to an exclusive-OR gate 62, with the result that a pulse waveform appears at the output of the gate, the width of whose pulses is proportional to the phase difference between the inputs. The output is applied to a gate 63 together with the output of a clock oscillator 64 so that bursts of pulses from the oscillator, of varying length according to the width of the pulses from the gate 62, are applied to a counter 66 associated with a digital display 68, the reading of which at the end of a period, conveniently the period P, provides a measure of the phase difference between the waveforms obtained from opposite sides of the brain. The counters 58 and 66 are conveniently cleared and disabled in the same manner and at the same time as the counters 22 and 26.

In use, the electrodes 2, 4, 6, 8 are applied to a subject, a good contact being assured by the use of conventional techniques such as placing brine soaked pads between the electrodes and the subject's skin. To operate the apparatus, the various counters and registers are reset by means of the manual reset 38 and the timer counter 36 is allowed to count off a period P whereupon the counters are disabled and the computing device is operated to provide a readout of neural efficiency as already described. Simultaneously, readouts are obtained indicating phase and amplitude differences between the waveforms from opposite sides of the brain. These readouts may be recorded and the process repeated several times for greater reliability and to check for repeatability. Preferably the output of one of the EEG amplifiers 10, 12 is applied to an artefact detector 70 driving a lamp indicator 72. The aretefact detector acts is known manner to detect the presence of high amplitude excursions at frequencies above 25 Hz, which usually are not due to normal brain function but commonly arise due to muscular tension in the subject or excessive pick-up of mains hum. Illumination of the indication will warn an operator to disregard a test during which the indicator is illuminated.

What I claim is:

1. A method of determining the average frequency of a sample of a band-limited EEG waveform in the presence of an intermittent interfering unwanted alpha rhythm waveform of relatively greater amplitude than the components of the wanted waveform and of a defined frequency range within said band limits, comprising sensing a subject's brain waveform, limiting said waveform to frequencies within said band limits, detecting in a sample of said waveform at least every alternate zero crossing point in the waveform, counting the events defined by adjacent alternate crossing points, identifying events having durations respectively within and outside a range corresponding to the duration of a cycle of a waveform within the defined frequency range of the unwanted waveform, determining the number and the sum of the durations of the events having durations outside said range during said sample, and calculating from said number and said sum the average frequency of these latter events.

2. A method according to claim 1, wherein said number and said sum are determined by determining the total number of events in the sample, deducting from this total the number of events having durations within said range, determining the duration of the sample and deducting the duration of those events having durations within said range from the duration of the sample, and the so reduced total of events is divided by the so reduced duration of the sample to calculate the average frequency of the EEG waveform.

3. A method according to claim 1, wherein the EEG waveform bandwidth is about 4–40 Hz and the unwanted waveforms have a frequency range of about 7-12 Hz.

4. A method of obtaining data relating to the brain function of a subject, comprising sensing, amplifying and band limiting the subject's brain waveform, detecting the presence of alpha rhythm in said waveform, discarding those portions of the waveform in which said alpha rhythm is present, and determining the average frequency of the remainder of the band limited waveform.

5. A method of providing data relating to the brain function of a subject comprising sensing the subject's brain waveform, amplifying and band limiting said waveform, sensing at least each alternate zero crossing of said waveform, sensing the number and duration of the time intervals between said alternate zero crossings, isolating those intervals whose combined duration corresponds to the cycle length of an alpha event, and ascertaining the mean duration of the remaining intervals whereby to determine the mean frequency of the band limited waveform when alpha events are not taking place.

6. A method according to claim 5, including sensing the subject's brain waveform from both sides of the brain simultaneously, similarly amplifying and band limiting both waveforms, comparing the mean amplitudes of the two amplified and band limited waveforms, and indicating the magnitude of any difference between said mean amplitudes.

7. A method according to claim 5, including sensing the subject's brain waveform from both sides of the brain simultaneously, similarly amplifying and band limiting both waveforms, comparing the relative phases of the two amplified and band limited waveforms, and indicating the magnitude of any phase difference between the waveforms.

8. Apparatus for determining the average frequency of non-alpha events in the brain waveform of a subject, comprising electrode means to sense a subject's brain waveform, an EEG amplifier receiving and amplifying signals from said electrode assembly, band limiting means receiving the output of said amplifier and operative to exclude unwanted components of the waveform, zero crossing detector means receiving said band limited signal and operative to detect at least each alternate zero crossing of the waveform so as to divide it into a series of events, means receiving the output of the zero crossing detector means and operative to detect which of said events have a duration corresponding to the periodicity of alpha rhythm, and means controlled by said output receiving means to collect sufficient data relating to the events detected thereby to define the average frequency of the non-alpha events.

9. Apparatus according to claim 8, including timer means to set a defined period wherein the data collection means includes means counting the total number of events in the defined period, means counting the total number of alpha events within the defined period, and means registering the total duration of the alpha events within said defined period.

10. Apparatus according to claim 9, wherein the data collection means includes computation means receiving the counts accumulated by said counting means and said registering means at the end of said defined period, and computing the average frequency of the non-alpha events to provide an output according to the following formula $$(N - Na)/(P - Na.aP)$$

where P is the defined period, N is the number of events in said period, Na is the number of alpha events in said period, and Na.aP is the total duration of the alpha events where aP is the average duration of the alpha events, and wherein a display means is associated with said computation means to display the output thereof.

11. Apparatus according to claim 9, wherein display means are associated with said counting means and said registering means to display their respective counts at the end of said defined period.

12. Apparatus according to claim 8, comprising duplicated electrode means, amplifiers, filters and zero crossing detectors, whereby to process signals from both sides of a subject's brain simultaneously, and further including a phase difference detector receiving the outputs of the two zero crossing detector means, and means to receive the output of the phase difference detector and display the phase differences detected thereby.

13. Apparatus according to claim 12, further including means to detect the difference in amplitude of the signals in the two channels, and means to receive the output of the amplitude difference detector and display the amplitude difference detected thereby.

* * * * *